(12) United States Patent
Bernardin et al.

(10) Patent No.: US 9,944,533 B2
(45) Date of Patent: Apr. 17, 2018

(54) INSTALLATION AND PROCESS FOR THE PREPARATION OF HYDROGEN CYANIDE

(71) Applicant: Arkema France, Colombes (FR)

(72) Inventors: Yves Bernardin, Thionville (FR); Xavier Marcarian, Billere (FR); Romain Billon, Carrieres sur Seine (FR)

(73) Assignee: Arkema France, Colombes (FR)

( * ) Notice: Subject to any disclaimer, the term of this patent is extended or adjusted under 35 U.S.C. 154(b) by 26 days.

(21) Appl. No.: 14/905,435

(22) PCT Filed: Jul. 18, 2014

(86) PCT No.: PCT/EP2014/065567
§ 371 (c)(1),
(2) Date: Jan. 15, 2016

(87) PCT Pub. No.: WO2015/007907
PCT Pub. Date: Jan. 22, 2015

(65) Prior Publication Data
US 2016/0194212 A1  Jul. 7, 2016

(30) Foreign Application Priority Data

Jul. 19, 2013  (FR) ...................... 13 57132

(51) Int. Cl.
*C01C 3/02* (2006.01)
*C07C 67/20* (2006.01)
*C07C 231/06* (2006.01)
*C07C 231/12* (2006.01)
*C07C 253/04* (2006.01)
*C07C 51/06* (2006.01)

(52) U.S. Cl.
CPC ............ *C01C 3/0212* (2013.01); *C01C 3/022* (2013.01); *C07C 51/06* (2013.01); *C07C 67/20* (2013.01); *C07C 231/06* (2013.01); *C07C 231/12* (2013.01); *C07C 253/04* (2013.01); *Y02P 20/129* (2015.11)

(58) Field of Classification Search
CPC ..... C01C 3/0212; C01C 3/022; C07C 231/06; C07C 23/12; C07C 253/04; C07C 51/06; C07C 67/20
See application file for complete search history.

(56) References Cited

U.S. PATENT DOCUMENTS

| | | | | |
|---|---|---|---|---|
| 2,803,522 | A |  | 8/1957 | Inman |
| 3,215,495 | A | * | 11/1965 | Andresen ................... B01J 8/02 422/211 |
| 3,667,907 | A | * | 6/1972 | Rushmere ............. C01C 3/0212 423/376 |
| 3,911,089 | A | * | 10/1975 | Shiraishi .............. B01J 23/8873 423/376 |
| 4,262,686 | A | * | 4/1981 | Heim ..................... A61M 16/12 137/101.19 |
| 6,075,162 | A | * | 6/2000 | Kida ..................... C01C 3/0241 558/332 |
| 6,221,327 | B1 |  | 4/2001 | DeCourcy et al. |
| 6,491,876 | B2 |  | 12/2002 | Cowell et al. |
| 6,596,251 | B2 | * | 7/2003 | Schaefer ............... C01C 3/0212 423/376 |
| 2010/0086468 | A1 |  | 4/2010 | Schaefer et al. |
| 2010/0166631 | A1 | * | 7/2010 | Schwefer ................. B01J 8/008 423/237 |
| 2011/0033362 | A1 | * | 2/2011 | Formentin ............ C01C 3/0212 423/372 |

* cited by examiner

*Primary Examiner* — Pancham Bakshi
*Assistant Examiner* — Mark R Luderer
(74) *Attorney, Agent, or Firm* — Thomas F. Roland

(57) ABSTRACT

Present invention relates to a process and an installation (100) for the preparation of hydrogen cyanide by the Andrussow process, and more precisely for improving the conditions of mixing the reactant gases before feeding the Andrussow type reactor (60), in order to improve safety, to avoid any risk of explosion and to produce HCN in safe and efficient manner. The installation is configured in such a manner that oxygen is pre-mixed with air with a ratio comprised between 20.95% and 32.5% by volume, preferably between 25% and 30.5% by volume; methane containing gas and ammonia are simultaneously added in the pre-mixture of oxygen-enriched air in such a manner that the volumic ratio of methane to ammonia is comprised between 1.35 and 1.02 depending on the content of oxygen into air; said obtained reactant gases mixture having a temperature comprised between 80° C. and 120° C., preferably between 95° C. and 115° C. for feeding the Andrussow type reactor (60).

8 Claims, 4 Drawing Sheets

INSTALLATION AND PROCESS FOR THE PREPARATION OF HYDROGEN CYANIDE

Figure 1:
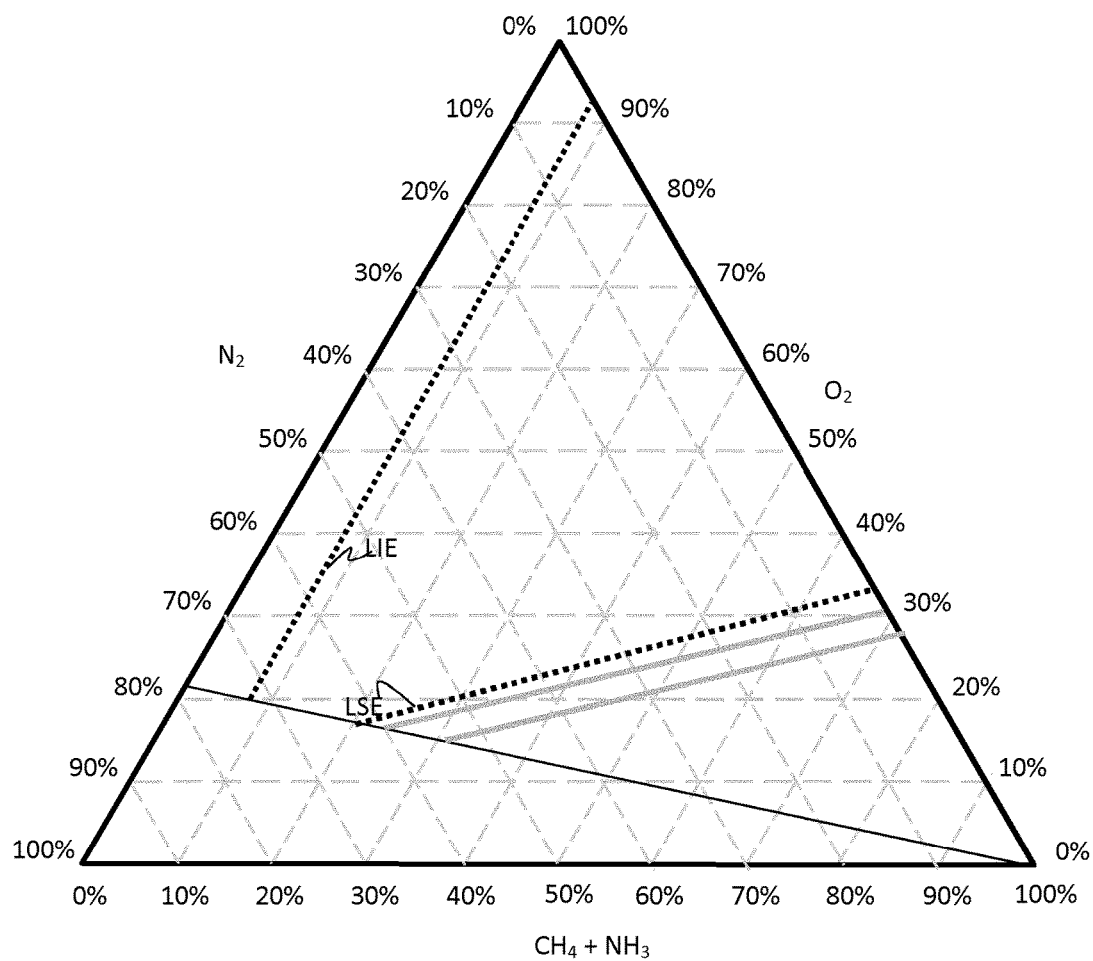

This application claims benefit, under 35 U.S.C. § 119 or § 365 of PCT Application Number PCT/EP2014/065567 filed Jul. 18, 2014; and French Application Number FR 13.57132, filed Jul. 19, 2013.

FIELD OF THE INVENTION

The present invention relates to an improvement of the Andrussow process for preparing hydrogen cyanide (HCN). It relates more particularly to an improved installation for preparing a mixture of reactant gases flowing through the input of an Andrussow type reactor, which contains catalysts gauzes over which the stream of reactant gases mixture flows and reacts to produce HCN.

STATE OF THE ART

Hydrogen cyanide HCN is the starting product for a number of organic and inorganic synthesis, leading for example to the following products: acetone cyanohydrin ACH, cyanuric chloride, adiponitrile, methionine, inorganic compounds such as sodium cyanide and the like, NTA (NiTriloAcetic acid) EDTA (EthyleneDiamineTetraAcetic acid) etc. . . . . When acetone cyanohydrin ACH is synthesized, it is used for example for the preparation of alkyl methacrylates or methacrylic acids. Such industrial processes for obtaining either alkyl methacrylates or methacrylic acids are made in a continuous manner, and each step of such processes has to be controlled very precisely in order to avoid stops due to safety problems relating for example to deflagration risks.

Andrussow's process is a well-known process and widely used for HCN synthesis by ammoxidation of methane. Hydrogen cyanide is obtained by the action of ammonia on methane in the presence of air over a catalyst consisting of platinum-rhodium gauzes. The reaction between ammonia and methane is the following:

$$CH_4 + NH_3 \rightarrow HCN + 3H_2 \tag{1}$$

Such a reaction is endothermic. Therefore, in absence of oxygen, it is necessary to mix a large quantity of methane compared to ammonia in order to burn the mixture and bring heat to enable the establishment of the reaction inside the reactor. The addition of air enables, thanks to the combustion of part of the hydrogen produced and excess of methane, to have a generally exothermic system and thus maintain the reaction synthesis without additional external energy. For that, the three reactant gases ($CH_4$, $NH_3$ and air) are mixed in precise volumic proportions. The resulting gas stream is introduced into an Andrussow type reactor. This reactor comprises catalyst gauzes made of platinum-rhodium placed on a support. A heat exchanger is placed downstream of the reactor for cooling the gas immediately after contact with the catalyst gauzes. The initiation of the reaction can be for example carried out with an electrical resistance which lights the gauzes. Once this ignition achieved, overall exothermic reactions maintains the gauzes at a temperature of about 750° C. to 1250° C., preferably 1000° C. to 1200° C.

The main reaction inside the reactor is the following:

$$CH_4 + NH_3 + 3/2\ O_2 \rightarrow HCN + 3H_2O \tag{2}$$

The mixture of air, methane-containing gas and ammonia is a flammable mixture and the exothermic reaction can lead to an explosion if the proportions of the reactant gases in the mixture are not precisely controlled and if the temperature of the mixture and the reaction are not controlled.

The document US2010/0086468 further discloses that the use of an oxygen-enriched air in the reactant gases mixture increases the reaction yield of production of HCN. However, this document makes safety issues more delicate to manage. Indeed, the disclosed ratio of oxygen to air is comprised between 20 and 100% by volume. Such a range is too large and it is much more awkward to mix pure oxygen or oxygen-enriched air with such high ratios of oxygen, with methane and ammonia, and feed an Andrussow type reactor with such a mixture and avoid having an explosion.

Although the Andrussow process for the preparation of HCN is known since a while, HCN is not so easy to prepare because the reactant gases ratios in the mixture have to be adjusted to avoid possible explosion. The temperature of the reactant gases mixture has also to be controlled in order to avoid an explosion of the mixture and a damage of the catalyst's gauzes of the reactor. Moreover, the reaction inside the Andrussow type reactor being exothermic, there is a risk of the apparition of a backfire from catalyst gauzes into the feeding pipe of the reactor.

The document WO97/09273 discloses a hydrogen cyanide process and apparatus therefore. The process uses an oxidant rich stream that contains from 30 to 100% by volume of oxygen. This oxygen rich stream is preheated to a temperature from 200° C. to 300° C. The other stream called feed stream is preheated to a temperature range from 300° C. to 450° C.

Therefore, there is a need of improving the safety of the continuous industrial process for production of HCN.

Technical Problem

Present invention aims to avoid at least one of the inconvenient of the state of the art. More particularly, the invention aims to propose a process and an installation for the preparation of hydrogen cyanide by the Andrussow process, and more precisely for improving the conditions of mixing the reactant gases before feeding the Andrussow type reactor, in order to improve safety of the continuous industrial process, to avoid emergency shutting down and any explosion and to produce HCN in safe, reliable and efficient manner.

BRIEF DESCRIPTION OF THE INVENTION

Surprisingly, it has been discovered that an installation for the preparation of hydrogen cyanide HCN, said installation comprising an Andrussow type reactor, in which is introduced a reactant gases mixture of methane-containing gas, ammonia and oxygen-enriched air, said mixture reacting inside said reactor over a catalyst to produce HCN, said installation comprising, upstream of said Andrussow type reactor according to the direction of gas flow, gas feeding pipes for feeding the installation with each reactant gas, a first unit for pre-mixing oxygen with air before adding methane-containing gas and ammonia into the obtained pre-mixture of oxygen-enriched air, said installation being characterized in that said first unit comprises at least one oxygen online controller so as to control the ratio of oxygen into air, said ratio having to be comprised between 20.95% and 32.5% in volume of oxygen, preferably between 25% and 30.5% in volume of oxygen; said installation comprising a second unit (U2) for adding simultaneously methane-containing gas and ammonia into the oxygen-enriched air with a volumic ratio of methane to ammonia, which has to be comprised between 1.35 and 1.02 depending on the proportion of oxygen into the oxygen-enriched air; said installation further comprising at least one heat exchanger for heating at least one of the reactant gases, in order to have a temperature of said reactant gases mixture feeding said Andrussow type reactor (60) comprised between 80° C. and 120° C. preferably between 95° C. and 115° C., leads in the production of a reactant gases mixture, ready to feed the Andrussow type reactor, which is completely safe and does not risk to explode.

The applicant has also discovered that a process for preparing hydrogen cyanide HCN by reacting, over a catalyst placed inside an Andrussow type reactor, a reactant gases mixture containing a methane-containing gas, ammonia and oxygen-enriched air, the process comprising, before feeding the Andrussow type reactor with the reactant gases mixture, a pre-mixing step of oxygen with air followed by a simultaneous addition of methane-containing gas and ammonia into the obtained pre-mixture of oxygen-enriched air, said process being characterized in that oxygen is pre-mixed with air with a ratio comprised between 20.95 and 32.5% by volume, preferably between 25 and 30.5% by volume; methane containing gas and ammonia are simultaneously added in the pre-mixture of oxygen-enriched air in such a manner that the volumic ratio of methane to ammonia is comprised between 1.35 and 1.02 depending on the content of oxygen into air; said obtained reactant gases mixture having a temperature comprised between 80 and 120° C., preferably between 95 and 115° C. for feeding the Andrussow type reactor, leads in the production of a reactant gases mixture, ready to feed the Andrussow type reactor, which is completely safe and does not risk to explode. Such process enables also to produce a mixture which leads to improve the yield of the reaction of production of HCN inside the reactor.

According to another aspect, the invention relates to a process for preparing a monomer selected from methacrylic acid and/or methylmethacrylate comprising the steps of:

preparing hydrogen cyanide HCN by an Andrussow process, preparing acetone cyanohydrin ACH from hydrogen cyanide and acetone, hydrolyzing acetone cyanohydrin ACH to produce an hydrolysis mixture comprising α-hydroxyisobutyramide (HIBAM), α-sulfatoisobutyramide (SIBAM), 2-methacrylamide (MACRYDE) and methacrylique acid (MAA), thermally converting said hydrolysis mixture into a cracker mixture to produce a mixture of 2-methacrylamide (MACRYDE) and methacrylic acid (MAA), reacting the cracker mixture with a material selected from methanol or water to produce respectively a monomer selected from methyl methacrylate (MMA) or methacrylic acid (MAA), and purifying said obtained methyl methacrylate (MMA) or methacrylic acid (MAA), said process being characterized in that the first step of the preparation of hydrogen cyanide HCN is processed according to the process described above, by using installation described above.

INTRODUCTION OF THE FIGURES

Figure 2:
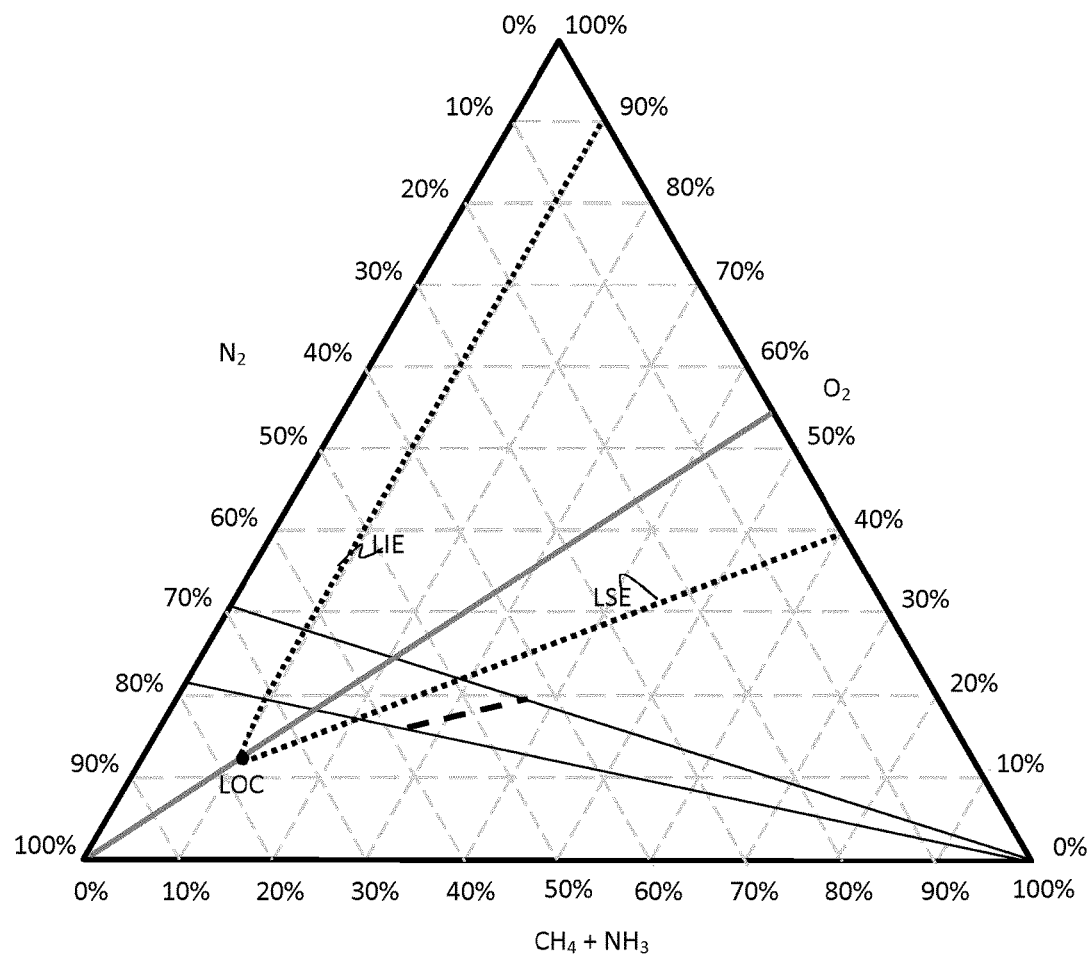
Figure 3:
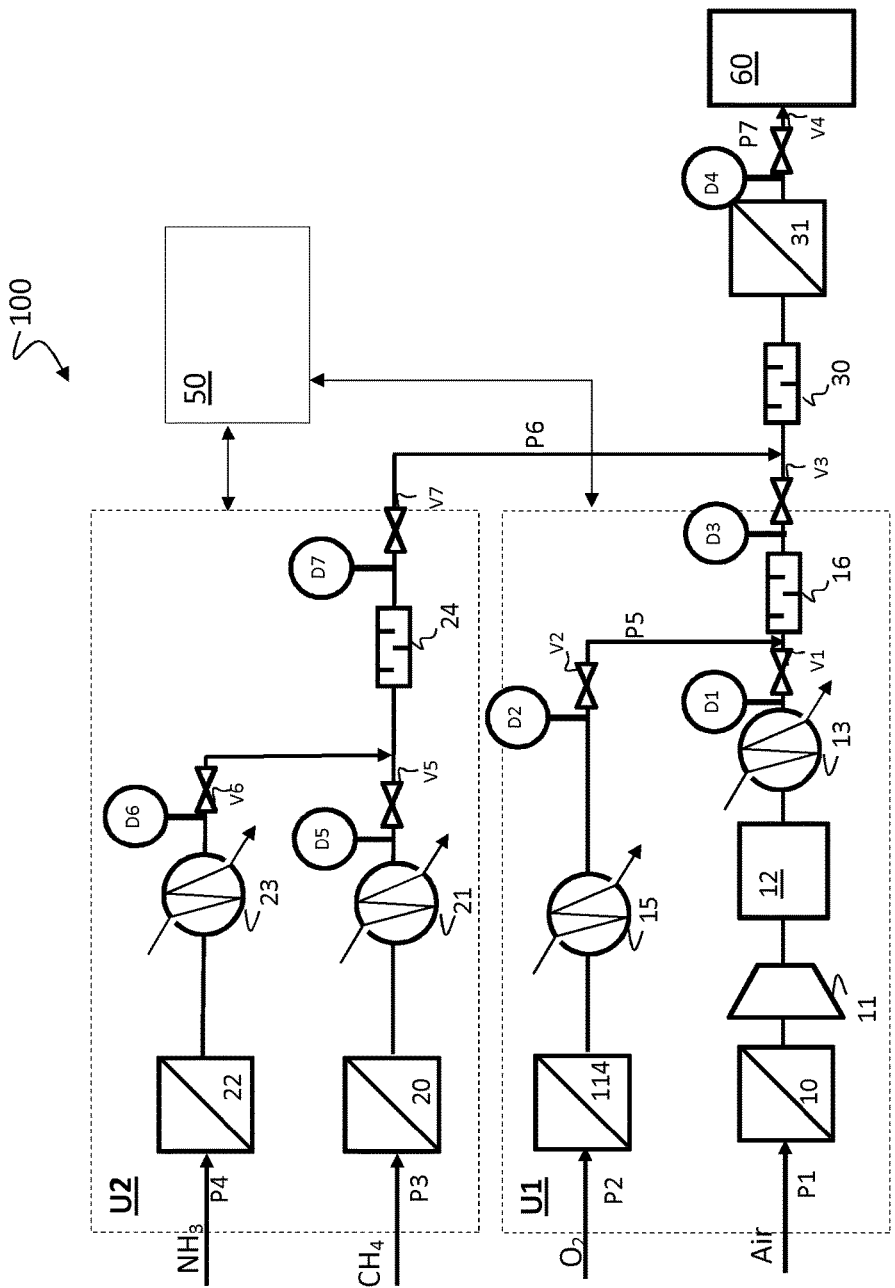
Figure 4:
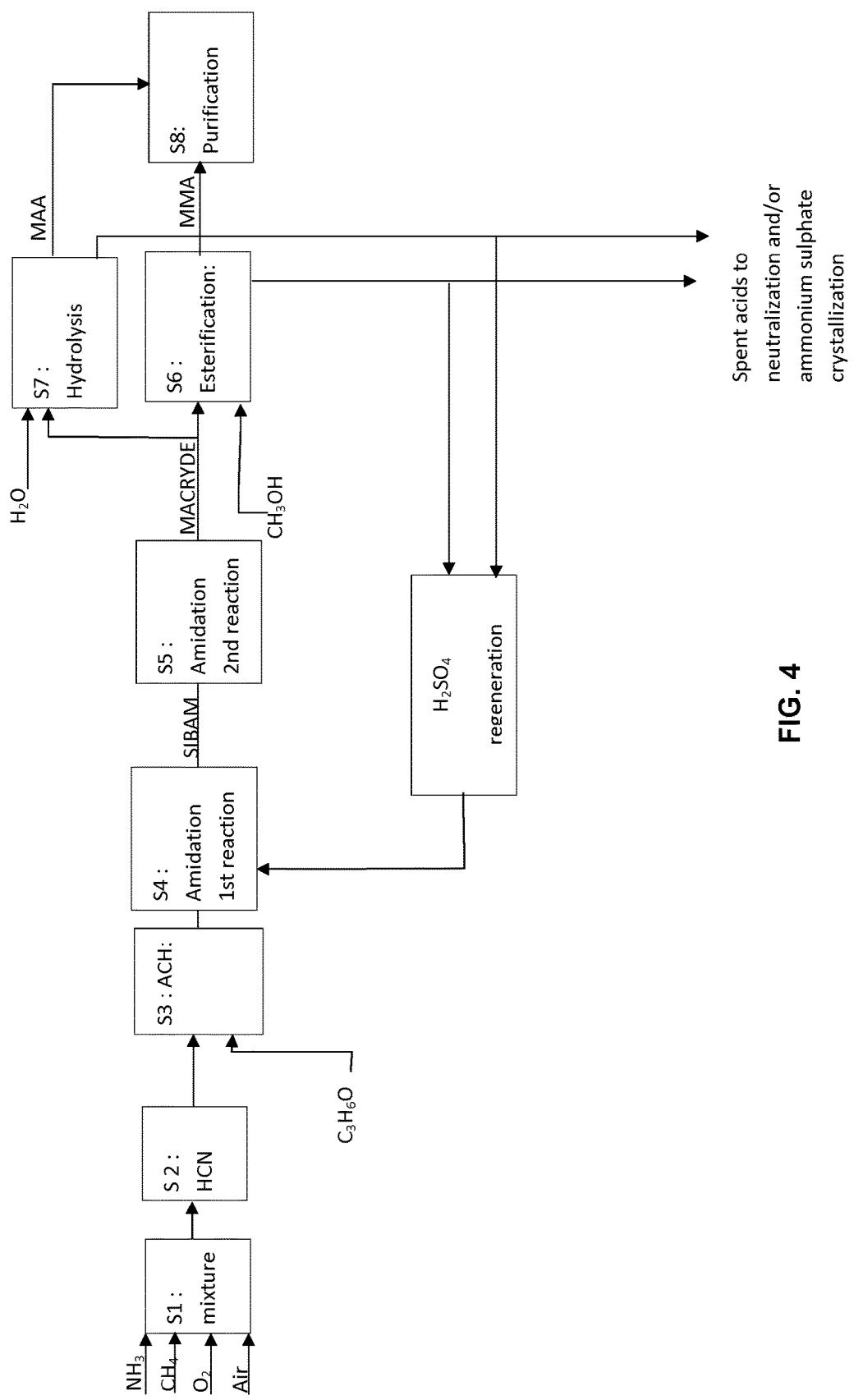

Other features and advantages of the invention will become apparent by reading the following description given by way of illustrative and non-limiting examples, with reference to the accompanying Figures in which:

FIG. 1 represents a ternary diagram of the reactant gas mixture composition for a volume ratio of methane to ammonia equal to 1, in a mixture according to prior art, FIG. 2 represents a ternary diagram of the reactant gas mixture composition for a volume ratio of methane to ammonia equal to 1.024 in a mixture according to the invention for avoiding explosion, FIG. 3 represents a schematic bloc diagram of an installation for preparation of the reactant gases mixture before its entering into the Andrussow type reactor, FIG. 4 represents a simplified schematic bloc diagram of a plant for preparing a monomer selected from methyl methacylates and/or methacrylic acids.

SPECIFICATION

Concerning the Preparation of HCN

FIG. 3 shows a schematic bloc diagram of an installation 100 used to prepare the reactant gas mixture before its entering into the Andrussow type reactor 60.

This installation 100 comprises four feeding pipes P1 to P4. A first feeding pipe P1 is dedicated for the feed of air, a feeding pipe P2 for the feed of oxygen, a third feeding pipe P3 for the feed of methane-containing gas, and the fourth feeding pipe P4 for the feed of ammonia.

Air is directly drawn up from the atmosphere and compressed, by means of a compressor referenced 11 on FIG. 3, to a pressure comprised between 1.4 and 3 bar (absolute pressure).

The installation 100 comprises a first unit, referenced U1 on FIG. 3, for premixing compressed air with oxygen in order to obtain a pre-mixture of an oxygen-enriched air. The proportion by volume of oxygen in relation to the total volume of air has to be precisely controlled in order to have a non-flammable pre-mixture. The proportion by volume of oxygen in relation to the total volume of air is advantageously selected in the range of 20.95% to 32.5%, and preferably between 25% to 30.5%.

It has been found that, with such composition, the safety problem is mastered and the flammability area is avoided if the other flow rate and thermodynamic parameters are also well controlled.

For a better comprehension, FIG. 1 shows a ternary diagram of the reactant gas composition in a mixture according to the previously cited document US 2010/0086468, and FIG. 2 shows a ternary diagram of the reactant gas composition in a mixture according to the invention. In the first diagram of FIG. 1, the two dotted lines represent respectively the lower (LIE) and higher (LSE) flammability limit for a mixture of methane and ammonia with a ratio equal to 1. The interval between the two grey lines corresponds to the operating area of the cited prior art. Such an operative area is too large because it authorizes to mix pure oxygen, or almost pure oxygen, with methane containing gas and ammonia. However such a mixture is not stable because flammable and it risks exploding at any time.

On the contrary, the invention limits the ratios of the reactant gases in the mixture in precise ratios in order to avoid the explosion area. The two black lines in the second diagram of FIG. 2, correspond to lines along which air comprises respectively 20.95% by volume of oxygen and 30.51% by volume of oxygen. Then between these two lines, an optimal safe operating area, which appears in dashed line on FIG. 2, is defined by further adjusting the ratios of methane and ammonia. The two dotted lines represent respectively the lower (LIE) and higher (LSE) flammability limit for a mixture of methane and ammonia with a ratio of 1.024. The grey line is a stoichiometric burn line. The point referenced LOC corresponds to oxygen concentration limit for the combustion of the mixture. Such limits may vary depending on the proportion of oxygen in the mixture, on the proportion of methane and ammonia, and on the temperature.

Therefore the selected optimal operating area along the dashed line is an optimal safe area for preparing the reactant gases mixture designed to be fed to the Andrussow type reactor for producing HCN. Such area is sure in terms of flammability and explosiveness.

Thus, at the beginning of the preparation of the reactant gases mixture, the first pre-mixture of air and oxygen is made by introducing progressively oxygen into compressed air in such a manner that the content of oxygen is progressively increased until reaching the maximum value of 32.5% by volume, and more preferably 30.5% by volume, in order to have an optimal productivity in safe conditions.

Such proportion of oxygen into air brings another advantage over prior art because less oxygen in air leads to an economic optimum.

In the unit U1 of the installation 100 (FIG. 3), the oxygen flow is regulated by some flow rate measurements, by means of flow rate controllers D1, D2, D3, by at least one oxygen online analyzer close to D3, and by some control valves V1 and V2 for example, which controls the proportion of oxygen to be added to the air and the composition of the oxygen-enriched air. There is an alarm in case of problems in the oxygen concentration, as the oxygen enrichment may vary between 20.95% and 32.5% by volume, and more preferably between 25% vol and 30.5% vol. Such alarm is connected to at least one safety valve V1, V2, V3, which is closed if the proportion of oxygen is not comprised into this range, and which stop the process. Such online controllers, alarm, safety valves, are all connected to a control unit 50, which manages the regulation of proportion of oxygen in air. For that, control unit determines all the set values of the gases ratios in the mixture and receives the measurements from the online analyzer(s), compares the measurements with the set values and manages all the safety devices if it detects an inconsistency in the results of the comparisons.

A static mixer 16 is preferably used to mix the obtained oxygen-enriched air in order to homogenize its composition.

Installation 100 comprises a second unit, referenced U2 on FIG. 3, for adding simultaneously methane-containing gas and ammonia into the oxygen-enriched air. Methane and ammonia have to be simultaneously added to the oxygen-enriched air for avoiding explosion. For that, the volumic ratio of methane to ammonia in the reactant gas mixture has to be precisely controlled in the range between 1.02 to 1.35, depending on the proportion of oxygen into oxygen-enriched air. Thus, if the proportion of $O_2$ into $O_2$-enriched air is 20.95% by volume, then the ratio of $CH_4/NH_3$ is 1.35 and if the proportion of $O_2$ into $O_2$-enriched air is 32.5% by volume, then the ratio of $CH_4/NH_3$ is 1.02.

As in the first unit U1, there is at least three flow rate measurements, by means of flow rate controllers D5, D6, D7, and some control valves V5 and V6 connected to the control unit 50, which manages the regulation of the flow rates of each gas, and at least one safety valve V5, V6, V7 in case if the proportions of $CH_4$ and $NH_3$ are not in the optimal safety operational area.

Preferably, the second unit U2 is a premixing unit for pre-mixing methane-containing gas with ammonia and for adding the obtained pre-mixture into the oxygen-enriched air. Before adding the pre-mixture of methane and ammonia into the oxygen-enriched airstream, the composition of said pre-mixture may also be homogenized in another static mixer 24. The addition of a homogeneous pre-mixture into the pre-mixture of oxygen-enriched air also advantageously avoids a local detonation point. However, in order to preserve costs, such a static mixer 24 may be not used.

A static mixer 30 is advantageously disposed on the feeding pipe, referenced P7, of the Andrussow type reactor 60, in order to homogenize the composition of the resultant reactant gas mixture, before its entry into the reactor 60. Such a homogenized composition, of the mixture of resultant reactant gas, avoids a local detonation point.

The installation comprises preferably a static mixer (30) designed to homogenize the composition of the reactant gases mixture before its introduction into the Andrussow type reactor (60) and advantageously it further comprises a second static mixer (16) designed to homogenize the composition of oxygen-enriched air before the addition of methane containing gas and ammonia.

For efficiency of the reaction the volumic ratio of oxygen-enriched air to ammonia is in the range between 7 (namely lower oxygen enrichment) to 3.5 (namely larger oxygen enrichment).

For flammability reasons, methane and ammonia feed volumic ratios are linked to the oxygen enrichment. More preferably, optimum parameters are linked according to following equations:

$$Y1=1.4745X-0.1611,$$

where Y1 is the molar $NH_3/O_2$-enriched air ratio and X is the molar $O_2/O_2$-enriched air ratio, and $$Y2=1.0406X-0.0234,$$

where Y2 is the molar $CH_4/O_2$-enriched air ratio and X is the molar $O_2/O_2$-enriched air ratio.

The control unit 50 is connected to an alarm and controls the ratios of $(O_2+air)/(CH_4)$ and of $(O_2+air)/(Ammonia)$ to avoid entering into a flammable zone. This range of proportion of oxygen is an economic compromise to limit quantity of nitrogen from air to be heated up during reaction and in the same time to limit pure oxygen or enriched air consumption. This leads also to a reduction of the amount of energy required to heat. Preparing an enriched air brings also advantages to reduce methane consumption, to increase productivity with reasonable size of equipment in reactor but also downstream the reactor, namely ammonia absorption column and HCN absorption column placed after the Andrussow type reactor.

Moreover, for safety reasons it is better first to heat each feed stream separately. Thus, each gas stream is independently preheated before its premixing with one another. Indeed, ammonia and methane-containing gas are independently preheated at a temperature between 60° C. and 100° C., by respective heaters 23 and 21, and oxygen and air are independently preheated at a temperature between 100° C. and 165° C., by means of respective heaters 15 and 13. Then, air and oxygen are premixed to control accurately enrichment. Ammonia and methane are premixed before mixing with enriched air. Such preheating of each gas enables to obtain a—resultant reactant gas mixture, at the output of the static mixer 30, having a temperature advantageously comprised between 80° C. and 120° C., preferably between 95° C. and 115° C. Such preheating and premixing of the gases avoids detonable mixture between either enriched air and ammonia or enriched air and methane. The temperature between 80° C. and 120° C., preferably between 95° C. and 115° C. for the resultant reactant gas mixture is an optimal zone of temperature to be sure to have a non-explosive gas mixture.

Moreover, the range of temperature between 80° C. and 120° C., preferably between 95° C. and 115° C. of the resultant reactant gas mixture, at the output of the static mixer 30, is a good compromise to avoid large excess of methane, so to improve $HCN/CH_4$ yield, and also to avoid making a detonable mixture.

Methane-containing gas is usually a natural gas, which is extracted from the underground, but methane containing gas can also come from other sources like for example petroleum industry (refineries, steam cracking), from biogas industry (fermentation), from coal industry (coal mine, coking). For safety reasons and in particular, for avoiding detonation and for avoiding damage of catalyst gauzes of the Andrussow type reactor, the purity of the methane has to be above 94% by volume. Indeed, the natural gas extracted from the underground may comprise sulphur components. However, sulphur components are pollutants for catalyst gauzes and reduce the number of active catalyst sites. It is however possible to clean the gas for purifying it and removing any residual concentration of sulphur components like mercaptans or hydrogen sulphide to proportions less than 5 ppm for each component and less than 20 ppm for total sulphur content. For that, a well-known desulfurization process can be used.

Furthermore, it is preferable to follow the methane-containing gas quality because an excess of hydrogen leads to an increase of the flammability risk, because hydrogen has not the same properties as methane in terms of burning and it is therefore difficult to control the flammability area. Moreover, an excess of alcene is pollutant for the catalyst gauzes of the Andrussow type reactor 60. Typically, the proportion of hydrogen has to be less than 3%, and the concentration of alkenes has to be less than 3500 ppm by volume. Consequently, an online analyzer (not shown) is advantageously placed on the feeding pipe P3, in order to follow the gas quality, especially the hydrogen and ethylene concentration.

According to another aspect of the invention, the resultant mixture of reactant gases flowing in the feeding pipe P7 of the Andrussow type reactor 60 shall have a controlled flow rate. Indeed, the flow rate of this mixture has to be higher than a minimum threshold value in order to avoid a backfire from the catalyst gauzes of the reactor, whose temperature is more than 750° C. Thus, the flow rate of the reactant gases mixture at the inlet of the Andrussow type reactor has to be higher than the flame velocity. The flame velocity mainly depends on the gas mixture composition, the temperature of the gas mixture and the feeding pipe P7 diameter. All gases are mixed in a single pipe P7 and flow across the static mixer 30, which homogenizes the composition of the mixture before feeding the reactor 60.

According to another aspect of the invention, to avoid carbamates formation between $CO_2$ (Carbone dioxide) from air and ammonia before gauzes of the reactor's catalyst, temperature of gas mixture must be over 70° C. Otherwise, air shall be washed with cool water at a temperature comprised between 15° C. and 30° C. Such washing thus improves catalyst gauzes life of the Andrussow type reactor.

Advantageously, steam may be added into the airstream before its premixing with oxygen. Such steam addition helps avoiding coke formation on catalyst gauzes of the Andrussow type reactor 60 and improves their lifetime. The steam addition enables also to moisten the air and to improve reaction performance. Steam flow rate is also controlled by a flow rate controller (not shown).

Such washing or steam addition is schematized by the same bloc referenced 12 on the FIG. 3. It is advantageously placed upstream the air heater 13.

Finally, for efficiency of reaction and more particularly for avoiding pollution of catalyst gauzes with dust or metallic oxides, it is better to provide a filtration device 10, 14, 20, 22 respectively on each feeding pipe P1 to P4. The resulting reactant gases mixture is also filtered by a filtration device 31. Such filtration devices on each gas stream allows to avoid pollution from pipes, of downstream process devices, like the reactor 60 and its catalyst gauzes, by removing solid particles, like iron for example, which is a precursor of coke. Indeed, iron oxide is a promoter for cracking methane, ammonia and also HCN. Thus, the decomposition reaction may lead to the formation of carbon (also called "coke"). After the last filtration 31, the gas mixture is sent to the Andrussow type reactor 60 for the synthesis of hydrogen cyanide HCN, at a temperature comprised between 750° C. and 1250° C., preferably between 1000° C. and 1200° C. and at an absolute pressure between 1.4 and 3 bar, and preferably between 2.2 and 2.4 bar.

Preferably, all the devices and units of the installation 100, such as pipes, safety valves, online controllers, filtering devices, heaters, air compressor etc. . . . are made of stainless steel. Such material is better than steel in terms of protection of catalyst gauzes. Indeed, when steel is used, an iron oxide based passivation layer, which is a pollutant for the catalyst gauzes, is formed in the devices. Such passivation layer does not appear with stainless steel.

The operating conditions that have been described above are a good compromise for improving $HCN/CH_4$ and $HCN/NH_3$ yields, while limiting oxygen amount relative to prior art and the related costs.

Synthesis of Monomer Selected from Methacrylic Acid and/or its Esters

FIG. 4 shows a simplified schematic block diagram of a plant for the production of methacylic acid and/or its esters from acetone and hydrogen cyanide HCN thus prepared by the Andrussow process. The Andrussow process is for example described in the document U.S. Pat. No. 1,934,838.

Such monomers can be further used to produce for example polymethylmethacrylate (PMMA) that is a polymer widely used in a lot of applications like for example automotive, transport, aerospace, photovoltaic, informatics, telecommunications, wind energy, or building construction . . . .

Preparation of Hydrogen Cyanide

First of all (steps S1 and S2) HCN is produced, from a mixture of methane-containing gas, ammonia and oxygen-enriched air. A mixture of reactant gases is prepared (step S1), by means of the installation described above, and introduced (step S2) into Andrussow type reactor 60 comprising catalyst gauzes based on platinum/rhodium gauzes. Mixture of gases passes over the catalyst gauzes and reacts at a temperature comprised between 750° C. and 1250° C., preferably between 1000° C. and 1200° C. to form HCN. The oxygen-enriched air enables to increase the productivity and to reduce the methane consumption. It facilitates also $NH_3$ absorption, HCN absorption and HCN distillation in downstream columns. The HCN produced is quickly cooled and treated so as to avoid polymerization of HCN. For that, ammonia which has not reacted is absorbed by reaction with sulfuric acid, and the HCN is absorbed and stabilized in an absorption column, and then distilled in a distillation column to reach a purity of 99,5% wt.

Preparation of Acetone Cyanohydrin

The thus synthesized HCN is then mixed with acetone ($C_3H_6O$), in step referenced S3, to produce acetone cyanohydrin ACH. The crude acetone cyanohydrin obtained is then purified by distillation.

Amidification of Acetone Cyanohydrin

In further steps (referenced S4, S5 in FIG. 4), the acetone cyanohydrin ACH prepared in the precedent step S3 is subjected to an amidification for producing 2-methacrylamide (also called "MACRYDE").

This amidification requires two steps S4 and S5 to reach the final product. First, in step S4, sulphuric acid ($H_2SO_4$) is added in excess in comparison with acetone cyanohydrin ACH. The molar ratio of $H_2SO_4$/ACH is comprised between 1.25 and 1.8, more preferably between 1.3 and 1.6.

The first reaction occurring is the hydrolysis of ACH by sulphuric acid which gives an intermediate salt called the SIBAM (for α-sulfatoisobutyramide). This reaction is the following:

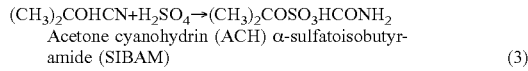
Acetone cyanohydrin (ACH) α-sulfatoisobutyramide (SIBAM)     (3)

This reaction is fast and exothermic. The temperature is around 80° C.-110° C. and the pressure is close to the atmospheric pressure.

The second reaction (step S5) is a slow and endothermic reaction. It occurs at atmospheric pressure and a temperature range between 110° C. and 165° C., preferably between 125° C. and 150° C. and more preferably between 130 and 145° C. This reaction is a cooking reaction which lasts between 3 and 16 minutes. This reaction is the following:

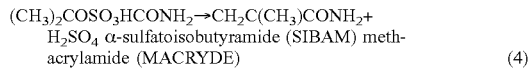
$H_2SO_4$ α-sulfatoisobutyramide (SIBAM) methacrylamide (MACRYDE)     (4)

During the synthesis reactions there are many other by-products. The main side reaction is described below.

The hydrolysis of ACH by water is very fast. A small quantity of water can create a significant quantity of HIBAM (α-hydroxyisobutyramide). This reaction is the following:

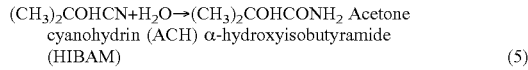
cyanohydrin (ACH) α-hydroxyisobutyramide (HIBAM)     (5)

In step S5, HIBAM can also create MACRYDE, but this reaction is very slow. So there is a large quantity of unconverted HIBAM at the end of amidification step S5. The reaction is the following:

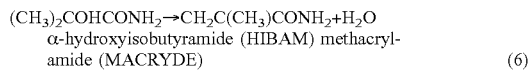
α-hydroxyisobutyramide (HIBAM) methacrylamide (MACRYDE)     (6)

The hydrolysis of HIBAM may create HIBA (α-hydroxyisobutyricacid):

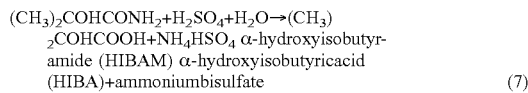
$_2$COHCOOH+NH$_4$HSO$_4$ α-hydroxyisobutyramide (HIBAM) α-hydroxyisobutyricacid (HIBA)+ammoniumbisulfate     (7)

At the same time, a significant amount of methacrylic acid MAA is produced by the hydrolysis of SIBAM by water. This reaction is the following:

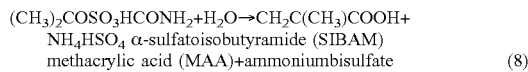
NH$_4$HSO$_4$ α-sulfatoisobutyramide (SIBAM) methacrylic acid (MAA)+ammoniumbisulfate     (8)

The mixture of MACRYDE and MAA obtained after amidification is then either hydrolyzed (step S7), by adding water to the MACRYDE, or esterified (step S6), by adding methanol to the MACRYDE.

Esterification

Then the components obtained after amidification, namely the methacrylamide and the methacrylic acid, are esterified, so as to obtain methylmethacrylate MMA. The esterification reaction (step S6) is made by mixing said components with methanol ($CH_3OH$).

The main reactions are these two below:

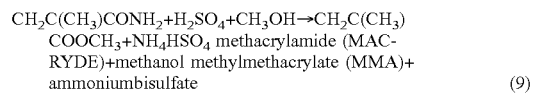
COOCH$_3$+NH$_4$HSO$_4$ methacrylamide (MACRYDE)+methanol methylmethacrylate (MMA)+ammoniumbisulfate     (9)

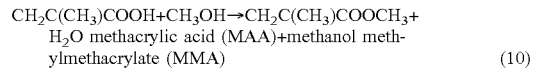
$H_2O$ methacrylic acid (MAA)+methanol methylmethacrylate (MMA)     (10)

Hydrolysis

The components obtained after amidification can also be hydrolysed by mixing them with water (step S7). Such hydrolysis reaction allows to obtain methacrylic acid according to the following reaction:

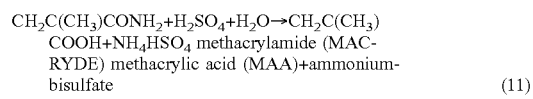
COOH+NH$_4$HSO$_4$ methacrylamide (MACRYDE) methacrylic acid (MAA)+ammoniumbisulfate     (11)

Purification of Crude MMA or MAA Obtained

Either the crude methylmethacrylate MMA obtained after esterification (S6) or the crude methacrylic acid MAA obtained after hydrolyse (S7) is then purified (step S8) by classical process known in the art, in order to remove residual compounds.

The invention claimed is:

1. A process for preparing hydrogen cyanide HCN by reacting, over a catalyst placed inside an Andrussow type reactor (60), a reactant gases mixture containing a methane-containing gas, ammonia and oxygen-enriched air, the process comprising before feeding the Andrussow type reactor with the reactant gases mixture, a pre-mixing step of oxygen with air followed by a simultaneous addition of methane-containing gas and ammonia into the obtained pre-mixture of oxygen-enriched air, said process comprising the steps of pre-mixing oxygen with air with a ratio comprised between 20.95% and 32.5% by volume, wherein the content of oxygen in air is progressively increased until reaching the maximum value of 32.5% by volume; simultaneously adding methane containing gas and ammonia in the pre-mixture of oxygen-enriched air in such a manner that the volumic ratio of methane to ammonia is comprised between 1.35 and 1.02 depending on the content of oxygen into air; said obtained reactant gases mixture having a temperature comprised between 80° C. and 120° C., for feeding the Andrussow type reactor (60).

2. The process according to claim 1, wherein the volumic ratio of oxygen-enriched air to ammonia is in the range between 7 to 3.5.

3. The process according to claim 1, wherein before pre-mixing, each gas is independently preheated, ammonia and methane-containing gas being independently preheated at a temperature between 60° C. and 100° C.; oxygen and air being independently preheated to a temperature between 100° C. and 165° C., so that the resultant reactant gas mixture, feeding the Andrussow type reactor, is at said temperature between 80° C. and 120° C.

4. The process according to claim 1, wherein the flow rate of the reactant gases mixture is controlled before feeding the Andrussow type reactor (60) so that it is higher than a predetermined threshold value, which depends on a flame velocity.

5. The process according to claim 1, wherein the methane-containing gas comprises methane of purity above 94% by volume.

6. The process according to claim 1, wherein before the preheating step and the premixing step of air with oxygen, and if the temperature of air is less than 70° C., air is washed with water, whose temperature is comprised between 15° C. and 30° C.

7. The process according to claim 1, wherein before the preheating step and the premixing step of air with oxygen, steam is injected into air stream.

8. The process according to claim 1, wherein each gas stream and the mixture of resultant reactant gases is filtered before feeding of Andrussow type reactor (60).

* * * * *